United States Patent [19]

Miura et al.

[11] Patent Number: 5,250,526
[45] Date of Patent: * Oct. 5, 1993

[54] PYRIDINECARBOXYLIC ACID AMIDE DERIVATIVES AND PHARMACEUTICAL COMPOSITIONS COMPRISING SAME

[75] Inventors: Katsutoshi Miura, Ohi; Hiroyasu Koyama, Ageo; Toshiji Sugai, Tsurugashima; Hiroaki Yamada; Einosuke Sakurai, both of Ohi; Masato Horigome, Tokyo, all of Japan

[73] Assignee: Nisshin Flour Milling Co., Ltd., Tokyo, Japan

[ * ] Notice: The portion of the term of this patent subsequent to Feb. 19, 2008 has been disclaimed.

[21] Appl. No.: 746,636

[22] Filed: Aug. 19, 1991

[30] Foreign Application Priority Data

Aug. 31, 1990 [JP] Japan ................................ 2-228381
Dec. 28, 1990 [JP] Japan ................................ 2-418550

[51] Int. Cl.⁵ ................. C07D 401/04; C07D 401/06; A61K 31/495; A61K 31/55
[52] U.S. Cl. ..................................... 514/218; 514/252; 540/575; 544/365; 546/316; 546/323
[58] Field of Search ................. 544/365; 540/575; 514/252, 218

[56] References Cited

U.S. PATENT DOCUMENTS 4,200,640  4/1980  Nagano et al. ....................... 514/355
4,780,560  10/1988  Kumonaka et al. ................ 558/482
4,994,456  2/1991  Miura et al. ......................... 544/364
5,025,012  6/1991  Miura et al. ......................... 544/364

FOREIGN PATENT DOCUMENTS 0385350  9/1990  European Pat. Off. .
62-205052  9/1987  Japan .
62-286968  12/1987  Japan .

OTHER PUBLICATIONS

Organic Synthesis, Collective vol. 3, E. C. Horning, ed., pp. 723-725, Roland Icke, et al., "β-Phenylethyldimethylamine" (1955).

*Primary Examiner*—Emily Bernhardt
*Attorney, Agent, or Firm*—Oblon, Spivak, McClelland, Maier & Neustadt

[57] ABSTRACT

Compounds are disclosed of the formula

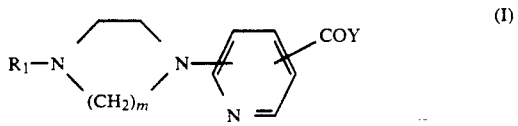

wherein $R_1$ is hydrogen, $C_1$-$C_3$ alkyl or diphenylmethyl; Y is $-NH(CH_2)_n-R_2$; $R_2$ is OH or $-ONO_2$; m is 2 or 3; and n is 9 to 13 or physiologically acceptable acid addition salts thereof. The compounds of formula (I) are of a blood flow-increasing and hypotensive actions and can be used for the therapy or prevention of diseases in the cardiovascular system.

10 Claims, No Drawings

PYRIDINECARBOXYLIC ACID AMIDE DERIVATIVES AND PHARMACEUTICAL COMPOSITIONS COMPRISING SAME

FIELD OF THE INVENTION

The present invention relates to new pyridinecarboxylic acid amide derivatives, a process for preparing the same and pharmaceutical compositions comprising said derivatives.

The pyridinecarboxylic acid amide derivatives and their physiologically acceptable salts of the invention possess an activity of increasing blood flow of vertebral, common carotid and femoral arteries and a hypotensive activity, which are effective in the therapy and prevention of disturbances of cerebral or peripheral circulation, ischemic heart diseases and hypertensions.

BACKGROUND OF THE INVENTION

Nicotinic acid amide derivatives useful as a therapeutic agent for cardiovascular diseases are disclosed in Japanese Patent Kokai No. 62-286968. Nitrate ester derivatives useful as vasodilator are also disclosed in Japanese Patent Kokai No. 62-205052. However, they are not satisfactory in efficacy as therapeutic agent for cardiovascular diseases. Thus there is a continuing need for new compounds with more improved pharmacological activities than known nicotinic acid amide derivatives.

The present invention results from efforts to develop new compounds possessing a high pharmacological activity, being readily available on an industrial scale and being satisfactory in practical use.

DISCLOSURE OF THE INVENTION

According to the invention, there are provided pyridinecarboxylic acid amide compounds of formula (I)

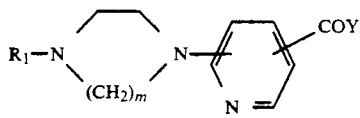
(I)

wherein $R_1$ is hydrogen, $C_1$-$C_3$ alkyl or diphenylmethyl;
Y is —NH(CH$_2$)$_n$—R$_2$;
R$_2$ is OH or —ONO$_2$;
m is 2 or 3; and n is 9 to 13; and physiologically acceptable acid addition salts thereof.

Examples of $R_1$ in formula (I) include hydrogen, methyl, ethyl, n-propyl, iso-propyl and diphenylmethyl.

Representative examples of the compounds according to the invention are as follows:
1) N-(12-hydroxy-1-dodecanyl)-6-(4-methyl-1-piperazinyl)nicotinamide,
2) N-(12-nitroxy-1-dodecanyl)-6-(4-methyl-1-piperazinyl)nicotinamide,
3) N-(11-hydroxy-1-undecanyl)-6-(4-diphenylmethyl-1-piperazinyl)nicotinamide,
4) N-(11-nitroxy-1-undecanyl)-6-(4-diphenylmethyl-1-piperazinyl)nicotinamide,
5) N-(9-hydroxy-1-nonyl)-6-(4-methyl-1-piperazinyl)nicotinamide,
6) N-(9-nitroxy-1-nonyl)-6-(4-methyl-1-piperazinyl)nicotinamide,
7) N-(10-hydroxy-1-decanyl)-6-(4-methyl-1-piperazinyl)nicotinamide,
8) N-(10-nitroxy-1-decanyl)-6-(4-methyl-1-piperazinyl)nicotinamide,
9) N-(11-hydroxy-1-undecanyl)-6-(4-methyl-1-piperazinyl)nicotinamide,
10) N-(11-nitroxy-1-undecanyl)-6-(4-methyl-1-piperazinyl)nicotinamide,
11) N-(11-hydroxy-1-undecanyl)-2-(4-ethyl-1-piperazinyl)nicotinamide,
12) N-(11-nitroxy-1-undecanyl)-2-(4-ethyl-1-piperazinyl)nicotinamide,
13) N-(11-nitroxy-1-undecanyl)-6-piperazinylnicotinamide.

The compounds of the invention can be prepared by reacting a compound of formula (II)

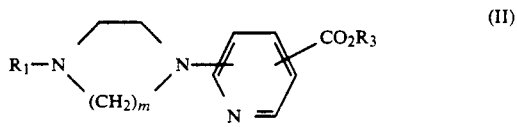
(II)

wherein $R_1$ and m are as defined above and $R_3$ is hydrogen or $C_1$-$C_6$ alkyl, with an amino compound of formula (III)

$$NH_2—(CH_2)_n—R_2 \quad (III)$$

wherein $R_2$ and n are as defined above and optionally subjecting the resulting reaction product where $R_2$ is OH to esterification with nitric acid to give a compound of formula (I)

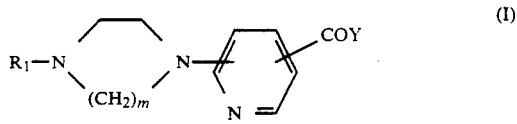
(I)

wherein $R_1$, Y and m are as defined above, or if necessary, converting the compound thus obtained to a physiologically acceptable acid addition salt.

Alternatively, the compounds of the invention can be prepared by reacting a compound of formula (IV)

(IV)

wherein X is halogen with a compound of the formula NH$_2$(CH$_2$)$_n$OH (n is 9-13) in an organic solvent to form a compound of the formula

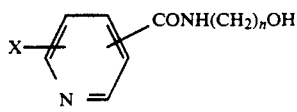

wherein X and n are as defined above and further condensing said compound with a compound of the formula

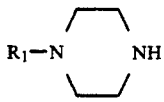

in the presence of an acid-binding agent to give a compound of formula (I) wherein Y is $-NH(CH_2)_n-OH$ or esterifying the resulting compound to give a compound of formula (I) wherein Y is $-NH(CH_2)_n-ONO_2$.

In case of using a compound of formula (II) wherein $R_3$ is $C_1-C_6$ alkyl, the reaction between a compound of formula (II) and a compound of formula (III) is effected using an excess amount of the compound of formula (III) with or without an organic solvent in the presence or absence of a catalyst such as 2-hydroxypyridine. The reaction is accomplished by stirring at a temperature between ordinary temperature and 150° C. for a period in the range from several tens minutes to several tens hours. Purification and isolation of the desired compounds are carried out by a conventional method. Thus a purified condensation product is obtained by extracting the reaction product with an organic solvent such as diethyl ether, ethyl acetate or dichloromethane, distilling off the extraction solvent from the extract and subjecting the residue to recrystallization or chromatography.

In cases where $R_2$ is OH in the condensation product obtained, a compound of formula (I) wherein $R_2$ is $ONO_2$ can be produced by mixing said condensation product with fuming nitric acid or a mixture of fuming nitric acid and acetic anhydride under ice-cooling and stirring the resulting mixture for 1-8 hours to form a nitrate ester.

In case of using a compound of formula (II) wherein $R_3$ is hydrogen, the compound (II) and an amino alcohol or its nitrate ester of formula (III) are subjected to condensation reaction in an organic solvent in the presence or absence of an appropriate amidating agent to form a compound of formula (I).

The reaction solvents used in these reactions include an aliphatic hydrocarbon such as n-hexane or petroleum ether; an aromatic hydrocarbon such as benzene, toluene or xylene; an alicyclic compound such as cyclohexane; a halogenated hydrocarbon such as carbon tetrachloride, chloroform, dichloroethane or trichloroethane; an aliphatic ketone such as acetone or methyl ethyl ketone; acetonitrile; N,N-dimethylformamide; dimethylsulfoxide or the like. Purification and isolation of the desired compounds are also carried out by a conventional method. Thus, a purified desired condensation product is obtained by distilling off the solvent after completion of the reaction, pouring the residue into an aqueous solution of sodium hydrogen carbonate, extracting the resulting mass with an organic solvent such as diethyl ether, ethyl acetate or dichloromethane, distilling off the extraction solvent from the extract and subjecting the residue to recrystallization or chromatography.

The compounds of formula (I) thus produced can be converted to acid addition salts thereof by a conventional method. The acid addition salts include acid addition salts of the compounds with an inorganic acid such as hydrochloric, sulfuric, phosphoric, hydrobromic or nitric acids, and acid addition salts of the compounds with an organic acid such as acetic, propionic, succinic, butyric, malic, citric, fumaric or tartaric acids.

The compound of formula (II) can be produced by condensing a compound of formula (V)

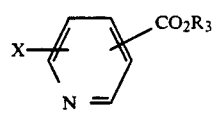

wherein X is halogen and $R_3$ is hydrogen or $C_1-C_6$ alkyl with a compound of formula (VI)

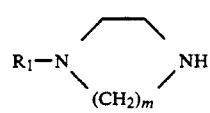

wherein $R_1$ is hydrogen, $C_1-C_3$ alkyl or diphenylmethyl and m is as defined above, in the presence of an acid-binding agent. In cases where $R_1$ in a compound obtained by the condensation reaction is hydrogen, if necessary, the compound and a compound of the formula $R_1-X$ wherein $R_1$ and X are as defined above may be reacted in an organic solvent in the presence of an acid-binding agent to give a compound of formula (II). In cases where $R_1$ in a compound obtained by the condensation reaction is hydrogen, the compound can be converted to a compound of formula (II) wherein $R_1$ is methyl by reaction with a mixture of formaldehyde and formic acid. This reaction can be accomplished under the reaction conditions described in Organic Synthesis Vol. 3, pages 723-725, which is incorporated herein by reference.

As clearly seen from the results of a pharmacological test shown below, the compounds of formula (I) of the invention exhibit marked blood flow-increasing and hypotensive actions in warm-blooded animals and can be used for the therapy or prevention of diseases in the cardiovascular system. Diseases in the cardiovascular system include disturbances of cerebral or peripheral circulation, ischemic heart diseases and hypertensions.

Thus, the invention further relates to pharmaceutical compositions for use in the therapy or prevention of the above-mentioned diseases, which comprise as an active ingredient a compound of formula (I) or a physiologically acceptable acid addition salt thereof.

The pharmaceutical compositions of the invention can orally or parenterally be administered in the suitable dosage forms. They can be administered alone, but are generally administered with a pharmaceutical carrier selected on the basis of the chosen route of administration and standard pharmaceutical practice. The dosage forms include tablets, capsules, suppositories, troches, syrups, creams, ointments, pasters, cataplasms, granules, powders, injections, suspensions and the like. Bi- or multi-layered tablets can also be prepared in combination with other drugs. Furthermore, tablets with conventional coating applied, for example, sugar-coated tablets, tablets with enteric coating or film-coated tablets can also be prepared.

In forming solid dosage forms there can be used additives such as lactose, white sugar, crystalline cellulose, corn starch, calcium phosphate, sorbitol, glycine, carboxymethyl cellulose, gum arabic, polyvinylpyrrolidone, hydroxypropyl cellulose, glycerin, polyethylene glycol, stearic acid, magnesium stearate and talc.

In forming semi-solid dosage forms, vegetable or synthetic waxes or fats and the like are used.

In forming liquid dosage forms, there can be employed additives such as an aqueous sodium chloride solution, sorbitol, glycerin, olive oil, almond oil, propylene glycol and ethyl alcohol.

The content of the active ingredient in the above dosage forms is in the range between 0.1 and 100% by weight, suitably between 1 and 50% by weight for oral administration and between 0.1 and 10% by weight for injection.

The dosage administered will, of course, vary depending upon the mode and route of administration, age, sex and weight of the patient, nature and extent of symptoms and the like. Usually a daily dosage of active ingredient can be about 1 to 1000 mg per kg of body weight.

The invention is further illustrated by the following non-limitative examples.

EXAMPLE 1

N-(12-hydroxy-1-dodecanyl)-6-(4-methyl-1-piperazinyl)nicotinamide

To 1.80 g of 6-chloronicotinic acid were added 1.0 ml of thionyl chloride and several drops of dimethylformamide and the mixture was refluxed under heat for 2 hrs. Excess thionyl chloride was distilled away to afford crystals of 6-nicotinic acid chloride. The crystals dissolved in 20 ml of tetrahydrofuran were added dropwise under ice-cooling to a solution of 1.39 g of 12-aminododecanol and 1.4 ml of triethylamine in 25 ml of tetrahydrofuran. The mixture was stirred overnight while elevating gradually to room temperature and the solvent was distilled away. The residue mixed with water was extracted with chloroform, washed with water and a saturated sodium chloride solution and dried over anhydrous magnesium sulfate. The solvent was distilled away to obtain N-(12-hydroxy-1-dodecanyl)-6-chloronicotinamide. This compound, 3.15 g of 1-methylpiperazine and 6.40 g of diisopropylamine were dissolved in 15 ml of p-xylene and a catalytic amount of sodium iodide was added to the solution which was stirred at 120°-130° C. for 5 hrs. This reaction mixture was poured into water, extracted with chloroform, washed with water and a saturated sodium chloride solution, dried over anhydrous magnesium sulfate and concentrated. The concentrate was purified by silica gel column chromatography (chloroform:methanol=20:1) to give 2.15 g (45%) of the title compound.

IR $\nu^{KBr}_{max}$(cm$^{-1}$) 3300, 1615, 1606

$^1$H-NMR(CDCl$_3$) δ 8.50 (1H, s), 7.89 (1H, d, J=8.0 Hz), 6.60 (1H, d, J=8.0 Hz), 6.25 (1H, m), 3.61 (6H, m), 3.38 (2H, m), 2.48 (4H, t, J=4.9 Hz), 2.33 (3H, s), 1.76–1.20 (20H,m)

EXAMPLE 2

N-(12-nitroxy-1-dodecanyl)-6-(4-methyl-1-piperazinyl)-nicotinamide 2.00 g of N-(12-hydroxy-1-dodecanyl)-6-(4-methyl-1-piperazinyl)nicotinamide were suspended in 40 ml of acetonitrile and to the suspension was added dropwise under ice-cooling a mixed solution of 0.8 ml of fuming nitric acid and 1.9 ml of acetic anhydride and stirred for 6 hrs. This reaction mixture was poured into an aqueous sodium hydrogencarbonate solution, extracted with methylene chloride, washed with water and a saturated sodium chloride solution, dried over anhydrous magnesium sulfate and concentrated to give 1.54 g (69%) of the title compound. m.p. 74°-76° C.

IR $\nu^{KBr}_{max}$(cm$^{-1}$) 3400, 1630, 1600

$^1$H-NMR (CDCl$_3$) δ 8.53 (1H, d, J=2.9 Hz), 7.89 (1H, dd, J=8.6, 2.9 Hz), 6.62 (1H, d, J=8.6 Hz), 5.97 (1H, m), 4.43 (2H, t, J=5.7 Hz), 3.67 (4H, t, J=5.7 Hz), 3.44 (2H, m), 2.50 (4H, t, J=5.7 Hz), 2.33 (3H, s), 1.85–1.20 (20H, m)

EXAMPLE 3

N-(11-hydroxy-1-undecanyl)-6-(4-diphenylmethyl-1-piperazinyl)nicotinamide

To 1.80 g of 6-chloronicotinic acid were added 1.0 ml of thionyl chloride and several drops of dimethylformamide and the mixture was refluxed under heat for 2 hrs. Excess thionyl chloride was distilled away to afford crystals of 6-nicotinic acid chloride. The crystals dissolved in 20 ml of tetrahydrofuran were added dropwise under ice-cooling to a mixture of 2.04 g of 11-aminoundecanol, 1.4 ml of triethylamine and 100 ml of tetrahydrofuran. The mixture was stirred overnight while elevating gradually to room temperature and the solvent was distilled away. The residue mixed with water was extracted with chloroform, washed with water and a saturated sodium chloride solution and dried over anhydrous magnesium sulfate. The solvent was distilled away to obtain N-(11-hydroxy-1-undecanyl)-6-chloronicotinamide. This compound, 2.88 g of 4-diphenylmethylpiperazine and 6.40 g of diisopropylamine were dissolved in 15 ml of p-xylene and a catalytic amount of sodium iodide was added to the solution which was stirred at 120°-130° C. for 5 hrs. This reaction mixture was poured into water, extracted with chloroform, washed with water and a saturated sodium chloride solution, dried over anhydrous magnesium sulfate and concentrated. The concentrate was purified by silica gel column chromatography (chloroform:methanol=20:1) to give 2.59 g (41%) of the title compound.

IR $\nu^{KBr}_{max}$(cm$^{-1}$) 3384, 1631, 1605, 1493

$^1$H-NMR (CDCl$_3$) δ8.51 (1H, d, J=2.4 Hz), 7.88(1H, dd, J=8.8, 2.4 Hz), 7.48-7.12 (10H, m), 6.56 (1H, d, J=8.8Hz), 6.10-5.98 (1H, m), 4.26(1H, s), 3.68-3.54 (6H, m), 3.46-3.32 (2H, m), 2.49 (4H, t, J=4.9 Hz), 1.76-1.20 (18H, m)

EXAMPLE 4

N-(11-nitroxy-1-undecanyl)-6-(4-diphenylmethyl-1-piperazinyl)nicotinamide 0.66 g of N-(11-hydroxy-1-undecanyl)-6-(4-diphenylmethyl-1-piperazinyl)nicotinamide were dissolved in 15 ml of methylene chloride and to the solution was added dropwise under ice-cooling a mixed solution of 0.2 ml of fuming nitric acid and 0.5 ml of acetic anhydride and stirred for 6 hrs. This reaction mixture was poured into an aqueous sodium hydrogencarbonate solution, extracted with methylene chloride, washed with water and a saturated sodium chloride solution, dried over anhydrous magnesium sulfate and concentrated. The concentrate was purified by silica gel column chromatography (hexane:ethyl acetate=2:1) to give 0.41 g (57%) of the title compound.

IR $\nu^{KBr}_{max}$(cm$^{-1}$) 3400, 1630, 1600

¹H-NMR(CDCl₃) δ 8.51 (1H, J=2.4 Hz), 7.88 (1H, dd, J=8.8, 2.4 Hz), 7.50-7.14 (10H, m), 6.57 (1H, d, J=8.8 Hz), 5.98-5.85 (1H, m), 4.43 (2H, t, J=6.6 Hz), 4.23 (1H, s), 3.62 (4H, t, J=4.9 Hz), 3.48-3.34 (2H, m), 2.49 (4H, t, J=4.9 Hz), 1.80-1.20 (18H, m)

EXAMPLE 5

N-(9-hydroxy-1-nonyl)-6-(4-methyl-1-piperazinyl)-nicotinamide

To 1.80 g of 6-chloronicotinic acid were added 1.0 ml of thionyl chloride and several drops of dimethylformamide and the mixture was refluxed under heat for 2 hrs. Excess thionyl chloride was distilled away to afford crystals of 6-nicotinic acid chloride. The crystals dissolved in 20 ml of tetrahydrofuran were added dropwise under ice-cooling to a solution of 2.55 g of 9-aminononanol and 1.4 ml of triethylamine in 25 ml of tetrahydrofuran. The mixture was stirred overnight while elevating gradually to room temperature and the solvent was distilled away. The residue mixed with water was extracted with chloroform, washed with water and a saturated sodium chloride solution and dried over anhydrous magnesium sulfate. The solvent was distilled away to obtain N-(9-hydroxy-1-nonyl)-6-chloronicotinamide. This compound, 3.15 g of 1-methylpiperazine and 6.40 g of diisopropylamine were dissolved in 15 ml of p-xylene and a catalytic amount of sodium iodide was added to the solution which was stirred at 120°-130° C. for 5 hrs. This reaction mixture was poured into water, extracted with chloroform, washed with water and a saturated sodium chloride solution, dried over anhydrous magnesium sulfate and concentrated. The concentrate was purified by silica gel column chromatography (chloroform:methanol=15:1) to give 2.48 g (60%) of the title compound.

IR $\nu^{KBr}_{max}$(cm⁻¹) 3400, 2950, 1640, 1600

¹H-NMR (CDCl₃) δ8.55 (1H, d, J=2.5 Hz), 7.90 (1H, dd, J=9.2, 2.3 Hz), 6.62 (1H, d, J=8.7 Hz), 6.20 (1H, m), 3.66 (6H, m), 3.44 (2H, m), 2.50 (4H, t, J=5.3 Hz), 2.34 (3H, s), 1.80-1.30 (14H, m)

EXAMPLE 6

N-(9-nitroxy-1-nonyl)-6-(4-methyl-1-piperazinyl)-nicotinamide 1.67 g of N-(9-hydroxy-1-nonyl)-6-(4-methyl-1-piperazinyl)nicotinamide were suspended in 40 ml of acetonitrile and to the suspension was added dropwise under ice-cooling a mixed solution of 0.8 ml of fuming nitric acid and 1.9 ml of acetic anhydride and stirred for 6 hrs. This reaction mixture was poured into an aqueous sodium hydrogencarbonate solution, extracted with methylene chloride, washed with water and a saturated sodium chloride solution, dried over anhydrous magnesium sulfate and concentrated to give 1.30 g (69%) of the title compound. m.p. 90°-92° C.

IR $\nu^{KBr}_{max}$(cm⁻¹) 3300, 1630, 1610

¹H-NMR(CDCl₃) δ8.55 (1H, d, J=2.9 Hz), 7.90 (1H, dd, J=8.8, 2.4 Hz), 6.63 (1H, d, J=8.8 Hz), 6.01 (1H, m), 4.46 (2H, t, J=6.3 Hz), 3.67 (4H, t, J=4.9 Hz), 3.47 (2H, m), 2.50 (4H, t, J=5.3 Hz), 2.33 (3H, s), 1.85-1.40 (14H, m)

EXAMPLE 7

N-(10-hydroxy-1-decanyl)-6-(4-methyl-1-piperazinyl)-nicotinamide

To 4.68 g of 6-chloronicotinic acid were added 5.0 ml of thionyl chloride and several drops of dimethylformamide and the mixture was refluxed under heat for 3 hrs. Excess thionyl chloride was distilled away to afford crystals of 6-nicotinic acid chloride. The crystals dissolved in 30 ml of tetrahydrofuran were added dropwise under ice-cooling to a solution of 5.15 g of 10-aminodecanol and 5.0 ml of triethylamine in 300 ml of tetrahydrofuran. The mixture was stirred overnight while elevating gradually to room temperature and the solvent was distilled away. The residue mixed with water was extracted with chloroform, washed with water and a saturated sodium chloride solution and dried over anhydrous magnesium sulfate. The solvent was distilled away to obtain N-(10-hydroxy-1-decanyl)-6-chloronicotinamide. This compound and 8.80 g of 1-methylpiperazine were dissolved in 50 ml of p-xylene and a catalytic amount of sodium iodide was added to the solution which was stirred at 130°-140° C. for 5 hrs. This reaction mixture was concentrated and the residue was purified by silica gel column chromatography (chloroform:methanol=15:1) to give 8.31 g (74%) of the title compound.

IR $\nu^{KBr}_{max}$(cm⁻¹) 3398, 3314, 1629, 1611

¹H-NMR (CDCl₃) δ 8.53 (1H, d, J=2.4 Hz), 7.90 (1H,dd, J=8.7, 2.3 Hz), 6.63 (1H, d, J=8.7 Hz), 6.02-5.90 (1H, m), 3.74-3.56 (6H, m), 3.50-3.36 (2H, m), 2.50 (4H, t, J=5.1 Hz), 2.35 (3H, s), 1.76-1.20 (16 H, m)

EXAMPLE 8

N-(10-nitroxy-1-decanyl)-6-(4-methyl-1-piperazinyl)-nicotinamide 6.00 g of N-(10-hydroxy-1-decanyl)-6-(4-methyl-1-piperazinyl)nicotinamide were added under ice-cooling to 20 ml of fuming nitric acid and the mixture was stirred below −5° C. for 4 hrs. This mixture was poured into an aqueous sodium hydrogencarbonate solution, extracted with methylene chloride, washed with eater and a saturated sodium chloride solution, dried over anhydrous magnesium sulfate and concentrated. The concentrate was purified by silica gel column chromatography (chloroform:methanol=20:1) and recrystallized from acetone-hexane to give 2.80 g (42%) of the title compound. m.p.62°-64° C.

IR $\nu^{KBr}_{max}$(cm⁻¹) 3320, 1624, 1604, 1279, 865

¹H-NMR (CDCl₃) δ 8.53 (1H, d, J=2.4 Hz), 7.90 (1H, dd, J=8.8, 2.4 Hz), 6.63 (1H, d, J=8.8 Hz), 5.98-5.86 (1H, m), 4.44 (2H, t, J=6.6 Hz), 3.66 (4H, t, J=5.1 Hz), 3.50-3.34 (2H, m), 2.50 (4H, t, J=5.1 Hz), 2.35 (3H, s), 1.80-1.20 (16H, m)

EXAMPLE 9

N-(11-hydroxy-1-undecanyl)-6-(4-methyl-1-piperazinyl)nicotinamide

To 6.24 g of 6-chloronicotinic acid were added 6.8 ml of thionyl chloride and several drops of dimethylformamide and the mixture was refluxed under heat for 3 hrs. Excess thionyl chloride was distilled away to afford crystals of 6-nicotinic acid chloride. The crystals dissolved in 40 ml of tetrahydrofuran were added dropwise under ice-cooling to a solution of 7.41 g of 11-aminoundecanol and 6.8 ml of triethylamine in 400 ml of tetrahydrofuran. The mixture was stirred overnight while elevating gradually to room temperature and the solvent was distilled away. The residue mixed with water was extracted with chloroform, washed with water and a saturated sodium chloride solution and dried over anhydrous magnesium sulfate. The solvent was distilled away to obtain N-(11-hydroxy-1- undecanyl)-6-chloronicotinamide. This compound and 11.70 g of 1-methylpiperazine were dissolved in 100 ml of p-xylene and a catalytic amount of sodium iodide was added to the solution which was stirred at 130°-140° C. for 5 hrs. This reaction mixture was concentrated and the residue was purified by silica gel column chromatography (chloroform:methanol=15:1) to give 10.12 g (65%) of the title compound.

IR $\nu^{KBr}_{max}$(cm$^{-1}$) 3316, 1629, 1611, 1497

$^1$H-NMR (CDCl$_3$) δ 8.53 (1H, d, J=2.4 Hz), 7.90 (1H, dd, J=8.8, 2.4 Hz), 6.62 (1H, d, J=8.8 Hz), 6.04–5.92 (1H, m), 3.70–3.65 (6H, m), 3.49–3.34 (2H, m), 2.50 (4H, t, J=5.1 Hz), 2.34 (3H, s), 1.72–1.20 (18H, m)

EXAMPLE 10

N-(11-nitroxy-1-undecanyl)-6-(4-methyl-1-piperazinyl)-nicotinamide 6.10 g of N-(11-hydroxy-1-decanyl)-6-(4-methyl-1-piperazinyl)nicotinamide were added under ice-cooling to 20 ml of fuming nitric acid and the mixture was stirred below −5° C. for 4 hrs. This mixture was poured into an aqueous sodium hydrogencarbonate solution, extracted with methylene chloride, washed with water and a saturated sodium chloride solution, dried over anhydrous magnesium sulfate and concentrated. The concentrate was purified by silica gel column chromatography (chloroform:methanol=20:1) and recrystallized from chloroform-hexane to give 5.47 g (80%) of the title compound.

m.p. 95°-96° C.

IR $\nu^{KBr}_{max}$(cm$^{-1}$) 3320, 1621, 1607, 1281, 867

$^1$H-NMR (CDCl$_3$) δ 8.53 (1H, d, J=2.4 Hz), 7.90 (1H, dd, J=8.8, 2.4 Hz), 6.63 (1H, d, J=8.8 Hz), 5.98–5.85 (1H, m), 4.44 (2H, t, J=6.8 Hz), 3.66 (4H, t, J=5.1 Hz), 3.50–3.36 (2H, m), 2.50 (4H,t, J=5.1 Hz), 2.35 (3H, s), 1.78–1.20 (18H, m)

EXAMPLE 11

N-(11-hydroxy-1-undecanyl)-2-(4-ethyl-1-piperazinyl)-nicotinamide

To 3.15 g of 2-hydroxy nicotinic acid were added 4.0 ml of thionyl chloride and several drops of dimethylformamide and the mixture was refluxed under heat for 2 hrs. Excess thionyl chloride was distilled away to afford crystals of 2-nicotinic acid chloride. The crystals dissolved in 30 ml of tetrahydrofuran were added dropwise under ice-cooling to a solution of 3.75 g of 11-aminoundecanol and 4.0 ml of triethylamine in 200 ml of tetrahydrofuran. The mixture was stirred overnight while elevating gradually to room temperature and the solvent was distilled away. The residue mixed with water was extracted with chloroform, washed with eater and a saturated sodium chloride solution and dried over anhydrous magnesium sulfate. The solvent was distilled away to obtain N-(11-hydroxy-1-undecanyl)-2-chloronicotinamide. This compound and 3.43 g of N-ethylpiperazine were dissolved in 30 ml of p-xylene and a catalytic amount of sodium iodide was added to the solution which was stirred at 130°-140° C. for 6 hrs. This reaction mixture was concentrated and the residue was purified by silica gel column chromatography (chloroform:methanol=20:1) to give 7.08 g (87%) of the title compound.

IR $\nu^{film}_{max}$(cm$^{-1}$) 3300, 1645, 1584

$^1$H-NMR (CDCl$_3$) δ 8.70–8.58 (1H, m), 8.36 (1H, dd, J=4.9, 2.0 Hz), 8.29 (1H, dd, J=7.5, 2.0 Hz), 7.07 (1H, dd, J=7.8, 4.9 Hz), 3.63 (2H, t, J=6.4 Hz), 3.52–3.36 (2H, m), 3.25 (4H, t, J=4.9 Hz), 2.61 (4H, t, J=4.9 Hz), 2.49 (2H, q, J=7.3 Hz), 1.72–1.22 (18H, m), 1.14 (3H, t, J=7.3 Hz).

EXAMPLE 12

N-(11-nitroxy-1-undecanyl)-2-(4-ethyl-1-piperazinyl)-nicotinamide 5.45 g of N-(11-hydroxy-1-undecanyl)-2-(4-ethyl-1-piperazinyl)nicotinamide were suspended in 100 ml of acetonitrile and to the suspension was added dropwise under ice-cooling a mixed solution of 2.0 ml of fuming nitric acid and 5.2 ml of acetic anhydride and stirred for 5 hrs. This reaction mixture was poured into an aqueous sodium hydrogencarbonate solution, extracted with methylene chloride, washed with water and a saturated sodium chloride solution, dried over anhydrous magnesium sulfate and concentrated. The concentrate was purified by silica gel column chromatography (chloroform:methanol=20:1) to give 2.52 g (42%) of the title compound.

IR $\nu^{film}_{max}$(cm$^{-1}$) 3300, 1657, 1631, 1280

$^1$H-NMR (CDCl$_3$) δ 8.70–8.56 (1H, m), 8.36 (1H, dd, J=4.9, 2.0 Hz), 8.29 (1H, dd, J=7.8, 2.0 Hz), 7.08 (1H, dd, J=7.8, 4.9 Hz), 4.443 (2H, t, J=6.6 Hz), 3.52–3.38 (2H, m), 3.26 (4H, t, J=4.9 Hz), 2.61 (4H, t, J=4.9 Hz), 2.49 (2H, q, J=7.3 Hz), 1.80–1.20 (18H, m), 1.14 (3H, t, J=7.3 Hz)

EXAMPLE 13

N-(11-nitroxy-1-undecanyl)-6-piperazinylnicotinamide 2.36 g of N-(11-hydroxy-1-undecanyl)-6-chloronicotinamide and 3.15 g of piperazine were suspended in 50 ml of toluene and the suspension was stirred at 120°-130° C. for 5 hrs. This reaction mixture was concentrated and the residue was purified by silica gel column chromatography (chloroform:methanol=5:1) to obtain quantitatively N-(11-hydroxy-1-undecanyl)-6-piperazinylnicotinamide. This compound was added under ice-cooling to 10 ml of fuming nitric acid and the mixture was stirred below 5° C. for 4 hrs. This reaction mixture was poured into an aqueous sodium hydrogencarbonate, extracted with methylene chloride, washed with water and a saturated sodium chloride solution, dried over anhydrous magnesium sulfate and concentrated. The concentrate was purified by silica gel column chromatography (chloroform:methanol=5:1) and recrystallized from chloroform/hexane to give 0.5 g (15%) of the title compound.

m.p. 78°-80° C.

$^1$H-NMR (CDCl$_3$) δ 8.54 (1H, d, J=2.0 Hz), 7.90 (1H, dd, J=8.8, 2.0 Hz), 6.64 (1H, d, J=8.8 Hz), 6.04–5.93 (1H, m), 4.44 (2H, t, J=6.8 Hz), 3.64 (4H, t, J=4.9 Hz), 3.42 (2H, dd, J=6.3, 6.3 Hz), 3.00 (4H, t, J=4.9 Hz), 1.75–1.64 (2H, m), 1.64–1.52 (2H, m), 1.44–1.20 (14H, m)

Blood flow-increasing and hypotensive actions were evaluated for the representative compounds of the invention by the method as described below.

Experimental method

Blood flow was measured unbloodily by means of an electromagnetic blood flow meter for right vertebral artery and right common carotide artery of the pentobarbital-anesthesized dog. Mean blood pressure was measured from a cannula in a femoral artery with a blood pressure transducer. The test compound was dissolved in a solution of ethanol/polyethyleneglycol 400/saline (1:1:2) and was intravenously administered at a dose of 0.1 mg/kg. The test results were expressed in terms of the percentage of post-administration change from the value prior to administration of a test compound, which are shown in the following table.

| Test Compound | Percent (%) Increase in Blood Flow | | Percent (%) Decrease in Mean Blood Pressure |
|---|---|---|---|
| | Vertebral artery | Common carotid artery | |
| Compound of Example 6 | +109 | +76 | −19 |
| Compound of Example 8 | +103 | +73 | −19 |
| Compound of Example 10 | +127 | +76 | −20 |

Useful pharmaceutical dosage-forms for administration of the compounds of this invention are illustrated below.

| Tablets (per tablet) | |
|---|---|
| Compound of Example 6 | 10 mg |
| Lactose | 67 mg |
| Crystalline cellulose | 15 mg |
| Corn starch | 7 mg |
| Magnesium stearate | 1 mg |
| | 100 mg |

The components were uniformly blended to prepare powders for direct tableting. The powders were formed by means of a rotary tableting machine to tablets 6 mm in diameter each weighing 100 mg.

| Granules (per pack) | |
|---|---|
| Compound of Example 6 (active ingredient) | 10 mg |
| Lactose | 90 mg |
| Corn Starch | 50 mg |
| Crystalline cellulose | 50 mg |
| Hydroxypropyl cellulose | 10 mg |
| Ethanol | 90 mg |

The active ingredient, lactose, corn starch and crystalline cellulose were uniformly blended and to the mixture were added hydroxypropyl cellulose and ethanol. The mixture was kneaded. The kneaded mass was graded by the extrusion granulating method and then dried in a drier at 50° C. The dried granules were screened to a mesh range between 297 μm and 1460 μm to prepare granules. One pack weighed 200 mg.

| Syrups | |
|---|---|
| Compound of Example 6 (active ingredient) | 1.000 g |
| White sugar | 30.000 g |
| D-Sorbitol 70 w/v % | 25.000 g |
| Ethyl paraoxybenzoate | 0.030 g |
| Propyl paraoxybenzoate | 0.025 g |
| Flavors | 0.200 g |
| Glycerin | 0.150 g |
| 96% Ethanol | 0.500 g |
| Distilled water | q.s. |
| Total | to 100 ml |

White sugar, D-sorbitol, methyl paraoxybenzoate, propyl paraoxybenzoate and the active ingredient were dissolved in 60 g of warm water. After cooling, a solution of the flavors in the glycerin and the ethanol was added. To the resulting mixture was added the water to 100 ml.

| Injections | |
|---|---|
| Compound of Example 6 (active ingredient) | 1 mg |
| Sodium chloride | 10 mg |
| Distilled water | q.s. |
| Total | to 1.0 ml |

Sodium chloride and the active ingredient were dissolved in distilled water to a total volume of 1.0 ml.

| Suppositories | |
|---|---|
| Compound of Example 6 (active ingredient) | 2 g |
| Polyethylene glycol 4000 | 20 g |
| Glycerin | 78 g |
| Total | to 100 g |

The active ingredient was dissolved in the glycerin. To the solution was added polyethylene glycol 4000 and the mixture was dissolved under heat. The solution was poured into a suppository mold to prepare suppositories each weighing 1.5 g.

What is claimed is:

1. A compound of formula (I)

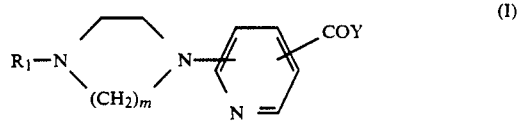

wherein $R_1$ is hydrogen, $C_1$-$C_3$ alkyl or diphenylmethyl; Y is $-NH(CH_2)_n-R_2$; $R_2$ is OH or $-ONO_2$; m is 2 or 3; and n is 9 to 13 or a physiologically acceptable acid addition salt thereof.

2. A compound of claim 1 wherein $R_1$ is methyl, ethyl, n-propyl or iso-propyl, Y is $-NH(CH_2)_n-OH$, n is 9 to 12 and m is 2.

3. A compound of claim 1 wherein $R_1$ is diphenylmethyl, Y is $-NH(CH_2)_n-OH$, n is 9 to 12 and m is 2.

4. A compound of claim 1 wherein $R_1$ is methyl, ethyl, n-propyl or iso-propyl, Y is $-NH(CH_2)_n-ONO_2$, n is 9 to 12 and m is 2.

5. A compound of claim 1 wherein $R_1$ is diphenylmethyl, Y is $-NH(CH_2)_n-ONO_2$, n is 9 to 12 and m is 2.

6. A pharmaceutical composition having blood flow-increasing and hypotensive actions which comprises a therapeutically effective amount of a compound of claim 1 or a physiologically acceptable addition salt thereof and a pharmaceutically acceptable carrier.

7. A pharmaceutical composition having blood flow-increasing and hypotensive actions which comprises a therapeutically effective amount of a compound of claim 2 or a physiologically acceptable addition salt thereof and a pharmaceutically acceptable carrier.

8. A pharmaceutical composition having blood flow-increasing and hypotensive actions which comprises a therapeutically effective amount of a compound of claim 3 or a physiologically acceptable addition salt thereof and a pharmaceutically acceptable carrier.

9. A pharmaceutical composition having blood flow-increasing and hypotensive actions which comprises a therapeutically effective amount of a compound of claim 4 or a physiologically acceptable addition salt thereof and a pharmaceutically acceptable carrier.

10. A pharmaceutical composition having blood flow-increasing and hypotensive actions which comprises a therapeutically effective amount of a compound of claim 5 or a physiologically acceptable addition salt thereof and a pharmaceutically acceptable carrier.

* * * * *